United States Patent [19]
Friebe et al.

[11] Patent Number: 5,447,934
[45] Date of Patent: Sep. 5, 1995

[54] ANTI-ALLERGIC THIADIAZOLO [4,3-A]PYRIDINE DERIVATIVES

[75] Inventors: Walter-Gunar Friebe, Mannheim; Henning Wilhelms, Weinheim/Rittenweier, both of Germany

[73] Assignee: Boehringer Mannheim GmbH, Mannheim, Germany

[21] Appl. No.: 204,391

[22] PCT Filed: Sep. 17, 1992

[86] PCT No.: PCT/EP92/02142

§ 371 Date: Mar. 18, 1994

§ 102(e) Date: Mar. 18, 1994

[87] PCT Pub. No.: WO93/06109

PCT Pub. Date: Apr. 1, 1993

[30] Foreign Application Priority Data

Sep. 23, 1991 [DE] Germany .................. 41 31 579.0

[51] Int. Cl.⁶ .................. A61K 31/435; C07D 513/04
[52] U.S. Cl. .................. 514/275; 514/293; 514/301; 544/331; 546/83; 546/114
[58] Field of Search .................. 546/83, 114; 544/331; 514/275, 293, 301

[56] References Cited

FOREIGN PATENT DOCUMENTS 2163427 2/1986 United Kingdom .

OTHER PUBLICATIONS

Potts et al. (I), J. Org. Chem. 35(6), pp. 1965–1968 (1970).
Potts, et al. (II) J. Org. Chem. 36(13), pp. 1846–1848 (1971).

Primary Examiner—Bernard Dentz
Attorney, Agent, or Firm—Nikaido, Marmelstein, Murray & Oram

[57] ABSTRACT

Compounds of the formula I

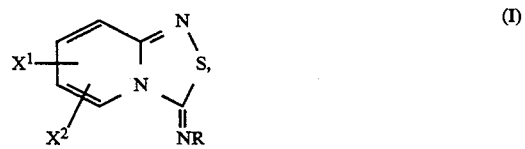

in which $X^1$ and $X^2$ the same or different, signify hydrogen, a $C_1$- to $C_6$-alkyl radical or a halogen atom or, insofar as they stand in neighbouring positions, together with the carbon atoms carrying them, form a condensed-on phenyl ring, and R signifies a possibly substituted carbocyclic or heterocyclic saturated or unsaturated radical, as well as their physiologically compatible salts, processes for their preparation, as well as medicaments which contain these compounds for the treatment of allergic diseases.

7 Claims, No Drawings

ANTI-ALLERGIC THIADIAZOLO [4,3-A]PYRIDINE DERIVATIVES

This application is a 371 of PCT/EP 92/02142.

The subject of the present invention are thiadiazolo[4,3-a]pyridine derivatives, processes for their preparation and medicaments which contain these compounds.

The invention concerns thiadiazolo[4,3-a]pyridine derivatives of the general formula I

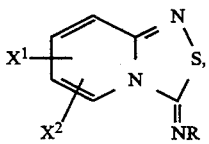

in which $X^1$ and $X^2$ the same or different, signify hydrogen, a $C_1$- to $C_6$-alkyl radical or a halogen atom or, insofar as they stand in neighbouring positions, together with the carbon atoms carrying them, form a condensed-on phenyl ring and R signifies a phenyl, cyclohexyl, cyclopentyl, pyridyl, piperidinyl, pyrimidinyl, pyrrolidinyl, isoxazolyl, oxazolyl, thiazolyl, thiazolinyl, thiazolyl or tetrazolyl radical which, if desired, can be substituted one or more times by halogen, cyano, nitro, $C_1$- to $C_6$-alkyl, $C_1$- to $C_6$-haloalkyl, hydroxyl, $C_1$- to $C_6$-alkoxy, methylenedioxy, $C_1$-$C_6$-alkylthio, $C_1$- to $C_6$-haloalkylthio, amino, $C_1$- to $C_6$-alkylamino, $C_2$- to $C_{12}$-dialkylamino, pyrrolyl, carboxy, carbamoyl, benzyl, $C_1$ to $C_6$-hydroxyalkyl, $C_2$- to $C_7$-carboxyalkyl, $C_2$- to $C_7$-alkoxycarbonyl-$C_1$-to $C_6$-alkyl, carbamoyl$_1$- to $C_6$-alkyl, N-hydroxy-N-$C_1$- to $C_6$-carbamoyl-$C_1$- to $C_6$-alkyl or $C_2$-to $C_6$-alkenyl, as well as their physiologically compatible salts, with the proviso that R cannot signify phenyl, 2,5-dichlorophenyl or 2-pyridinyl when $X^1$ and $X^2$ are simultaneously hydrogen or R cannot signify 3,4-dichlorophenyl when $X^1$ or $X^2$ represent methyl or R cannot signify 2-pyridinyl when $X^1$ or $X^2$ represents bromine.

Surprisingly, it was found that the compounds of the formula I display valuable pharmacological properties. In particular, they can inhibit the antigen-caused contraction of lung tissue strips. Therefore, they are suitable for the treatment of allergic diseases, as well as of inflammation-caused bronchospastic and bronchoconstrictory reactions.

Furthermore, they can prevent the lethality of an endotoxic shock and area therefore, suitable for the treatment of inflammatory processes brought about by monokines, as well as of septic shock, autoimmune diseases, graft-versus-host reactions and host-versus-graft diseases.

In J. Org. Chem. 35, 1965 (1970) is described inter alia the compound 3-(2-pyridinylimino)-3H-[1,2,4]-thiadiazolo[4,3-a]pyridine, in J. Org. Chem. 36, 1846 (1971) the compounds 3-phenylimino-3H-[1,2,4]thiadiazolo[4,3-a]pyridine and 3-(4-methylphenylimino)-3H-[1,2,4]-thiadiazolo4,3-a]pyridine but without statement of a pharmacological effectiveness. These compounds are also usable as medicaments and are the subject of the invention.

The alkyl radicals in the said alkyl, alkoxy, alkylthio and (di)alkylamino groups, as well as the alkenyl radicals, can be straight-chained or branched. Preferred alkyl radicals in these groups are the methyl, ethyl, n-propyl, isopropyl, n-butyl, isobutyl, tert.-butyl, n-pentyl and 3-pentyl radical, preferred alkenyl radicals the vinyl and the allyl radical.

A $C_1$-$C_6$-haloalkyl radical is preferably trifluormethyl.

As halogen atoms, there come into question fluorine, chlorine and bromine.

Carbocyclic radicals are preferably the phenyl, cyclohexyl and cyclopentyl radical. As heterocyclic radicals, there come into question especially pyridyl, piperidinyl, pyrimidinyl, pyrrolidinyl, isoxazolyl, oxazolyl, thiazolyl, thiazolinyl, triazolyl and tetrazolyl radicals.

Preferred compounds of the formula I are compounds in which $X^1$ represents hydrogen, methyl or chlorine, $X^2$ hydrogen or $X^1$ and $X^2$ together form a condensed-on phenyl ring and R a phenyl ring which can be substituted once or twice by fluorine, chlorine, methyl, methoxy, tert.-butyl, isopropoxy, trifluoromethyl, trifluoromethylthio, hydroxyl, nitrile, nitro, hydroxymethyl, methylenedioxy, diethylamino, methylthio, pyrrolyl, methoxycarbonylmethyl, carboxymethyl, N-hydroxy-N-methylcarbamoylmethyl or N-tetrazolylcarbamoylmethyl, or a thiazolyl, pyridinyl, tetrazolyl, pyrimidinyl or cyclohexyl radical.

Apart from the compounds mentioned in the Examples the subject of the invention are especially all substances which have every possible combination of the substituents mentioned in the Examples.

The process according to the invention for the preparation of the compounds of the formula I is characterised in that, in per se known way, one reacts a compound of the general formula II

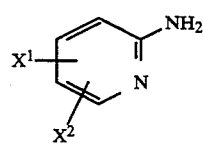

in which $X^1$ and $X^2$ have the above-mentioned meaning, either a) with a compound of the formula III $$ClSCCl_3 \qquad (III)$$

or a reactive derivative thereof and, a compound of the general formula IV $$H_2N\text{-}R \qquad (IV)$$

in which R has the above-mentioned meaning, or
b) with a compound of the general formula V
$$YS\text{-}CY=N\text{-}R \qquad (V)$$

in which R has the abovementioned meaning and Y represents a halogen atom, and subsequently, if desired, converts a radical R into another radical given by the definition and, if desired, converts the compound obtained of the formula I into a salt by reaction with physiologically compatible acids or bases.

As halogen atom for Y, there come into question especially chlorine and bromine.

One preferably so carries out the process according to the invention that one first condenses a compound of the general formula II with a compound of the formula III and isolates the product obtained. This intermediate product is then brought to reaction with a compound of the general formula IV.

Another variant consists in that the reaction mixture obtained from the reaction of a compound of the formula II with 8 compound of the formula III is, without isolation of the intermediate product, allowed to react with a compound of the formula IV The reaction expediently bakes place in a solvent, such as water, ether, a lower alcohols, such as for example methanol or ethanol, or a halogenated hydrocarbon, such as dichloromethane or trichloromethane, with addition of a base, such as triethylamine or sodium carbonate, at temperatures between −20° and 50° C., preferably between 0° C. and room temperature.

The compounds of the formulae II, IV and V are known from the literature or can easily be prepared according to trivial methods starting from known compounds.

A conversion of a radical R into another radical R takes place, for example, by ether cleavage with a proton acid or Lewis acid, such as hydrobromic acid, hydrochloric acid, hydrogen iodide, alnminium trichloride, boron tribromide, or by alkylation of a hydroxyl group with the desired alkyl halide or alkyl sulphate.

A carboxy group contained in R can, if desired, be converted into an ester group or carboxamide function via a reactive derivative, such as a halide, imidazolide or arthydride; an ester group contained in R can be converted by acidic or basic hydrolysis into the carboxy group, by aminolysis into the carboxamide group.

As pharmacologically compatible salts, there come into question especially alkali metal, alkaline earth metal and ammonium salts, as Well as possible salts with non-toxic inorganic or organic acids, such as e.g. hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

One obtains the salts in the usual way, e.g. by neutralisation of the compounds of the formula I with the appropriate lyes or acids.

For the preparation of medicaments, the compounds of the general formula I are mixed in per se usual way with suitable pharmaceutical carrier substances, aroma, flavouring and colouring materials and formed, for example, as tablets or dragees or, with addition of appropriate adjuvants, suspended or dissolved in water or oil, such as e.g. olive oil. oil.

The substances of the general formula I can be administered orally or parentally in liquid or solid form. As injection medium, water is preferably used which contains stabilising agents, solubilising agents and/or buffers usual in the case of injection solutions. Such additives are e.g. tartrate or borate buffers, ethanol, dimethyl sulphoxide, complex formers (such as ethylenediamine-tetrascetic acid), high molecular polymers (such as liquid polyethylene oxide) for the viscosity regulation or polyethylene derivatives of sorbitol anhydrides.

Solid carrier materials are e.g., starch, lactose, mannitol, methyl cellulose, talc, highly dispersed silicic acid, high molecular polymers (such as polyethylene glycols).

Compositions suitable for oral administration can, Q if desired, contain flavouring and sweetening agents. For the external use, the substances I according to the invention can also be used in the form of powders end salves. For this purpose, they are mixed e.g. with powdered, physiologically compatible dilution agents or usual salve bases.

The administered dose depends upon the age, the state of health and the weight of the recipient, the extent of the disease, the nature of further treatments possibly carried Out simultaneously, the frequency of the treatments and the nature of the desired action. Usually, the daily-dose of the active compound amounts to 0.1 to 50 mg/kg of body weight. Normally, 0.5 to 40 and preferably 1.0 to 20 mg/kg/day in one or more administrations per day are effective in order to obtain the desired results.

Apart from the substances mentioned in the Examples, in the meaning of the present invention the following compounds are preferred:
1. 4-(3H-[1,2,4]-thiadiazolo[4,3-a]pyridin-3-ylideneamino)-phenylacetic acid N-(1H-terazol-5-yl)-amide
2. 3-(2-pyrimidinylimino)-3H-[1,2,4]-thiadiazolo[4,3-a]-pyridine
3. 5-methyl-3-(4-pyridinylimino)-3H-[1,2,4]-thiadiazolo[4,3-a]pyridine
4. 6-methyl-3-(4-pyridinylimino)-3H-[1,2,4]-thiadiazolo[4,3-a]pyridine
5. 8-methyl-3-(4-pyridinylimino)-3H-[1,2,4]-thiadiazolo[4,3-a]pyridine.

EXAMPLE 1

3-(Thiazol-2-ylimino)-3H-[1,2,4]-thiadiazolo[4,3-a]pyridine

To a solution of 6.6 ml. (60 mmol) trichloromethanesulphenic acid chloride in 900 ml chloroform one adds dropwise at 0° C. a solution of 5.6 g (60 mmol) 2-aminopyridine and 8.3 ml triethylamine in 50 ml chloroform. One after-stirs for 10 min. and adds dropwise thereto a solution of 6.0 g (60 mmol) 2-aminothiazole and 25 ml triethylamine in 100 ml chloroform. After 3 h stirring at room temperature, one evapovates and washes the precipitate with methanol. There remain 8.9 g of title compound (63% of theory) of the m.p. 169°–171° C.

EXAMPLE 2

In a way analogous to that described in Example 1, from trichloromethanesulphenic acid chloride, 2-aminopyridine and the amine in question one obtains:

| designation | yield % | melting point °C. (solvent) |
|---|---|---|
| a) 3-(2-pyridinylimino)-3H-[1,2,4]-thiadiazolo [4,3-a]-pyridine from 2-amino-pyridine | 80 | 159–161 (ether) |
| b) 3-(4-pyridinylimino)-3H-[1,2,4]-thiadiazolo [4,3-a]-pyridine from 4-amino-pyridine | 37 | 185–186 (ethanol) |
| c) 3-phenylimino-3H-[1,2,4]-thiadiazolo [4,3-a]-pyridine from aniline | 67 | 84–86 (2-propanol) |
| d) 3-(4-chlorophenylimino)-3H-[1,2,4]-thiadiazolo [4,3-a]-pyridine from 4-chloro-aniline | 64 | 129–130 (2-propanol) |
| e) 3-(4-methoxyphenylimino)-3H-[1,2,4]-thiadiazolo-[4,3-a]pyridine from 4-methoxyaniline | 69 | 90–92 (2-propanol) |
| f) 3-(4-cyanophenylimino)-3H-[1,2,4]-thiadiazolo [4,3-a]-pyridine from 4-amino- | 57 | 149–150 (2-propanol) |

| designation | yield % | melting point °C. (solvent) |
|---|---|---|
| benzonitrile | | |
| g) 3-(4-nitrophenylimino)-3H-[1,2,4]-thiadiazolo [4,3-a]pyridine from 4-nitroaniline | 63 | 198–199 (2-propanol) |
| h) 3-cyclohexylimino-3H-[1,2,4]-thiadiazolo [4,3-a]-pyridine hydrochloride from cyclohexylamine | 28 | 194–196 (ethyl acetate) |
| i) 5-(5-1H-tetrazolylimino)-3H-[1,2,4]-thiadiazolo-[4,3-a]pyridine from 5-amino-IH-tetrazole | 29 | 282–283 (water) |
| j) 3-(4-fluorophenylamino)-3H-[1,2,4]-thiadiazolo-[4,3-a]-pyridine from 4-fluoroaniline | 67 | 138–140 (2-propanol) |
| k) 3-(2,4-dichlorophenyl-imino)-3H-[1,2,4]-thiadiazolo [4,3-a]pyridine from 2,4-dichloroaniline | 51 | 130–132 (2-propanol) |
| l) 3-(4-methylphenylimino)-3H-[1,2,4]-thiadiazolo-[4,3-a]pyridine from 4-methylaniline | 59 | 106–108 (2-propanol) |
| m) 3-(3-trifluoromethylphenyl-imino)-3H-[1,2,4]-thiadiazolo [4,3-a]pyridine from 3-trifluoromethylaniline | 34 | 48–49 (2-propanol) |
| n) 3-(2-hydroxymethylphenyl-imino)-3H-[1,2,4]-thiadiazolo [4,3-a]pyridine from 2-aminobenzyl alcohol | 49 | 118–119 (2-propanol) |
| o) 3-(2-hydroxyphenylimino)-3H-[1,2,4]-thiadiazolo-[4,3-a]pyridine from 2-aminoyphenol | 21 | 130–132 (2-propanol) |
| p) 3-(4-hydroxy-2-methyl-phenylimino)-3H-[1,2,4]-thiadiazolo [4,3-a]-pyridine from 4-amino-3-methylphenol | 49 | 241–243 (2-propanol) |
| q) 3-(3,4-methylenedioxyphenyl-imino)-3H-[1,2,4]-thiadiazolo [4,3-a]-pyridine from 3,4-methylenedioxyaniline | 49 | 141–143 (2-propanol) |
| r) 3-(3-trifluoromethylthio-phenylimino)-3H-[1,2,4]-thiadiazolo [4,3-a]pyridine from 3-trifluoromethylaniline | 70 | 86–88 (2-propanol) |
| s) 3-(4-diethylaminophenyl-imino)-3H-[1,2,4]-thiadiazolo [4,3-a]pyridine from N,N-diethyl-1,4-phenylenediamine | 54 | 96–97 (2-propenol) |
| t) 3-(5-methylisoxazol-3-yl-imino)-3H-[1,2,4]-thiadiazolo [4,3-a]pyridine from 3-amino-5-methylisoxazole | 36 | 170–172 (2-propanol) |
| u) 3-(4,5-dihydrothiazol-2-ylimino)-3H-[1,2,4]-thiadiazolo [4,3-a]pyridine from 2-amino-2-thiazoline | 55 | 106–108 (2-propenol) |
| v) 3-(1-benzylpiperidin-4-ylimino)-3H-[1,2,4]-thiadiazolo [4,3-a]pyridine from 4-amino-1-benzyl-piperidine | 55 | 90–92 (2-propanol) |
| w) 3-(3-pyridinylimino)-3H-[1,2,4]-thiadiazolo-[4,3-a]-pyridine from 3-aminopyridine | 67 | 133–134 (2-propanol) |
| x) 3-(4-t-butylphenylimino)-3H-[1,2,4]-thiadiazolo-[4,3-a]pyridine from 4-t-butylaniline | 46 | 72–74 (isohexane) |
| y) 3-(4-isopropoxyphenyl-imino)-3H-[1,2,4]-thiadiazolo [4,3-a]pyridine from 4-isopropoxyaniline | 52 | 94–95 (ether) |
| z) 3-(4-methylthiophenyl-imino)-3H-[1,2,4]-thiadiazolo [4,3-a]pyridine from 4-methylmercaptoaniline | 76 | 111–112 (2-propanol) |
| aa) 3-(4-pyrrolidinophenyl-imino)-3H-[1,2,4]-thiadiazolo [4,3-a]pyridine from N-(4-aminaphenyl)-pyrrole | 68 | 167–168 (ethyl acetate) |

EXAMPLE 3

7-Methyl-3-(4-pyridinylimino)-3H-[1,2,4]-thiadiazolo-[4,3-a]pyridine

To a solution of 3.3 ml (30 mmol) trichloromethane-sulphenic acid chloride in 450 ml dichloromethane one adds dropwise at 0° C. a solution of 3.2 g (30 mmol) 2-amino-4-methylpyridine and 4.2 ml triethylamine in 25 ml. dichloromethane, stirs for 10 min and adds dropwise thereto a solution of 2.8 g (30 mmol) 4-aminopyridine and 12 ml triethylamine in 100 ml dichloromethane. After 3 h stirring at room temperature, one pours into water, extracts with ethyl acetate, dries the extract, evaporates and chromatographs on silica gel (elution agent ethyl acetate/isohexane 1:1), One isolates 1,2 g of title compound (17% of theory) of the m.p. 144°–145° C.

EXAMPLE 4

6-Chloro-5(4-pyridinylimino)-3H-1,2,4]-thiadiazolo-[4,3-a]pyridine

In analogous way to that described in Example 3, one obtains the title compound with 20% yield of the m.p. 205°–207° C. from 2-amino-5-chloropyridine and 4-aminopyridine.

EXAMPLE 5

5-Phenylimino-3H-[1,2,4]-thiadiazolo[4,3a-]quinoline

To a solution of 3.1 g (21 retool) 2-aminoquinoline and 6 ml triethylamine in 70 ml dichloromethane one adds dropwise at 0° C., a solution of 4.1 g (21 mmol) 1-chloro-1-phenyliminomethanesulphenic acid chloride in 20 ml dichloromethane, stirs for 5 h at room temperature, washes the organic phase with water, dries, evaporates and chromatographs on silica gel. With isohexene/ethyl acetate 9:1, one elutes 2.3 g of title compound (39% of theory) of the m.p. 116°–118 ° C.

EXAMPLE 6

3-(4-pridinylimino)-3H-[1,2,4]-thiadiazolo[4,3-quinoline

In an analogous way to that described in Example 3, one obtains the title compound with 11% yield of the m.p. 180°–182° C. from 2-aminoquinoline and 4-aminopyridine.

EXAMPLE 7

3-(4-Methoxycarbonylmethylphenylimino)-3H-[1,2,4]-thiadiazolo[4,3-a]pyridine In an analogous way to that described in Example 1, one obtains the title compound with 41% yield of the m.p. 151°614 152° C. (from ethyl acetate) from 2-aminopyridine and 4-aminophenylacetic acid methyl ester.

EXAMPLE 8

4-(3H/[1,2,4]-Thiadiazol[4,3-a]-pyridin-3-ylindeneamino)-phenylacetic acid N-methylhydroxamide A mixture of 9.0 g (30 mmol) of the compound of Example 7, 100 ml ethanol and 500 mI N hydrochloric acid is stirred for 6 h at 50° C. One evaporates and triturates the residue with acetone. There remain 8.9 g of title compound (92% of theory) of the m.p. 209°–211° C.

EXAMPLE 9

4-(3H-[1,2,4]-Thiadiazole[4,3-a]-pyridin-3-ylideneamino)-phenylacetic acid N-methylhydroxamide To a mixture of 4.8 g (15 mmoI) of compound of Example 8, 90 ml dichloromethane and 1 ml dimethylformamide one adds dropwise at 0° C. a solution of 1.7 ml oxalyl chloride in 15 ml dichloromethane. The solution obtained is stirred for 40 min and subsequently added dropwise to a solution of 5.0 g N-methylhydroxylamine in 15 ml triethylamine, 10 ml of water and 60 ml tetrahydrofursn. After 50 min stirring, one mixes with 20 ml of water, extracts with dichloromethane, dries, evaporates and purifies on silica gel (elution agent trichloromethane/methanol 95:5). One isolates 3.4 .g of title compound (78% of theory) which, after trituration with ether, melts at 135°–136° C.

Test Report

Inhibition of the antigen-caused construction of passive sensitised guinea pig lung parenchyma strips in vitro (organ bath)

For the in vitro investigation of the compounds according to the invention, the inhibition of the antigen-caused constriction of passive sensitised guinea pig lung parenchyma strips was measured, as described in the following:

Pirbright white guinea pigs were stunned by a blow to the nape of the neck and exsanguinated. The lungs were rinsed substantially blood-free in situ with Krebs buffer, pH 7.4. Subsequently, the lungs were removed, cut up into strips (about 20×4a 4 mm) and the strips passively sensitised for one hour at room temperature with a 1.:50 dilution of a homologous anti-ovalbumin antiserum and then washed with Krebs buffer 1 x. The antiserum had been previously produced according to DAVIES (1) in guinea pigs of the same strain by repeated injection of ovalbumin (2 x crystallised) with addition of complete Freund's adjuvant. Until its used the antiserum was stored undiluted at −18° C. Subsequently, the lung strips were individually suspended on an isometric measurement sensor in 10 ml waterbaths with an initial tension of 1.2 g. Thereafter, the baths were filled with Krebs buffer and continuously gassed at 37° C. with $O_2$ (95%) and $CO_2$ (5%). Via an amplifier the constrictions of the lung strips were recorded on a recorder. After 30 minutes acclimatisation phase, histamine control spasms were produced for the recognition of the reactivity of the organ pieces washed, subsequently the best substance preincubated 37° C. for 20 minutes and thereafter the ovalbumin-caused constriction initiated. The inhibition action of the compounds according to the invention was expressed as percentage reduction of the constriction amplitude of the "samples with best substance" in relation to the "untreated control constrictions".

(1) DAVIS, G. E., T. P. Johnstone Quantitative studies on anaphylaxis in guinea pigs passively sensitised with homologous antibody. Inter., Arch. Allergy 41, 648–454 (1971).

TABLE

% Inhibition of the constriction of passive-sensitised lung parenchyms strips (guinea pigs) induced by ovalbumin (0.1 µg/ml).
20 min/37°C. preincubation time (organ bath technique)
n = number of the tests
+ = 200 µg/ml.

| substance Example No. | concentration (10 µg/ml) | n |
|---|---|---|
| aminophylline | 26+ | 6 |
| 2a) | 56 | 3 |
| 2b) | 80 | 2 |
| 2e) | 48 | 3 |
| 2p) | 62 | 3 |
| 2q) | 57 | 3 |
| 2u) | 78 | 4 |
| 4 | 61 | 3 |
| 9 | 61 | 3 |

We claim:

1. A compound of the formula

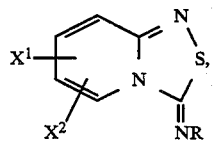

(I)

wherein $X^1$ and $X^2$ are the same or different and independently are hydrogen, $C_1$–$C_6$ alkyl or halogen, or, if on adjacent ring carbon atoms, together with the adjacent ring carbon atoms, form a condensed phenyl ring, and R is a radical selected from the group consisting of phenyl, cyclohexyl, cyclopentyl, 3-pyridyl, 4-pyridyl, piperidinyl, pyrimidinyl, pyrrolidinyl, isoxazolyl oxazolyl thiazolyl, thiazolinyl, triazolyl and tetrazolyl, which radical is unsubstituted or substituted at least once by halogen, cyano, nitro, $C_1$–$C_6$ alkyl, $C_1$–$C_6$ haloalkyl, hydroxyl, $C_1$–$C_6$ alkoxy, methylenedioxy, $C_1$–$C_6$-alkylthio, $C_1$–$C_6$ haloalkylthio, amino, $C_1$–$C_6$ alkylamino, $C_2$–$C_{12}$ dialkylamino, pyrrolyl, carboxyl, carbamoyl, benzyl, $C_1$–$C_6$ hydroxyalkyl, $C_1$–$C_7$ carboxyalkyl, $C_2$–$C_7$ alkoxycarbonyl-$C_1$–$C_6$-alkyl, carbamoyl-$C_1$–$C_6$-alkyl, N-hydroxy-N-$C_1$–$C_6$ alkyl carbamoyl-$C_1$–$C_6$-alkyl or $C_2$–$C_6$ alkenyl, or a physiologically compatible salt thereof, provided, however, that when $X^1$ and $X^2$ are both hydrogen then R is other than phenyl, 4-methylphenyl or 2,5-dichlorophenyl, and that when $X^1$ or $X^2$ represent methyl, R is not 3,4-dichlorophenyl.

2. Compound of claim 1, wherein $X^1$ is hydrogen, methyl or chlorine, $X^2$ is hydrogen, or $X^1$ and $X^2$ form part of a condensed phenyl ring, and R is a phenyl ring which is unsubstituted or substituted once or twice by fluorine, chlorine, methyl, methoxy, tert.-butyl, isopropoxy, trifluoromethyl, trifluoromethylthio, hydroxyl, nitrile, nitro, hydroxymethyl, methylenedioxy, diethylamino, methylthio, pyrrolyl, methoxycarbonylmethyl, carboxymethyl, N-hydroxy-N-methylcarbamoylmethyl or N-tetrazolylcarbamoylmethyl, or R is a thiazolyl, pyridinyl, tetrazolyl, pyrimidinyl or cyclohexyl radical.

3. Compound of claim 1, wherein the compound is
3-(4-pyridinylimino)-3H-[1,2,4]-thiadiazolo[4,3-a]-pyridine,
3-(4-chlorophenylimino)-3H-[1,2,4]thiadiazolo[4,3-a]-pyridine,
3-(4-methoxyphenylimino)-3H-[1,2,4]-thiadiazolo-[4,3-a]pyridine,
3-(4-cyanophenylimino)-3H-[1,2,4]-thiadiazolo[4,3-a]-pyridine,
3-(4-nitrophenylimino)-3H-[1,2,4]-thiadiazolo[4,3-a]-pyridine,
3-cyclohexylimino-3H-[1,2,4]-thiadiazolo[4,3-a]-pyridine hydrochloride,
3-(5-1H-tetrazolylimino)-3H-[1,2,4]-thiadiazolo-[4,3-a]-pyridine,
3-(4-fluorophenylamino)-3H-[1,2,4]-thiadiazolo-[4,3-a]-pyridine,
3-(2,4-dichlorophenylimino)3H-[1,2,4]-thiadiazolo[4,3-a]-pyridine,
3-(3-trifluoromethylphenylimino)-3H-[1,2,4]-thiadiazolo[4,3a]-pyridine,
3-(2-hydroxymethylphenylimino)-3H-[1,2,4]-thiadiazolo[4,3-a]-pyridine,
3-(2-hydroxyphenylimino)-3H-[1,2,4]-thiadiazolo-[4,3-a]-pyridine,
3-(4-hydroxy-2-methyl-phenylimino)-3H-[1,2,4]-thiadiazolo[4,3-a]-pyridine,
3-(3,4-methylenedioxyphenylimino)-3H-[1,2,4]-thiadiazolo[4,3a]-pyridine,
3-(3-trifluoromethylthiophenylimino)-3H-[1,2,4]thiadiazolo[4,3-a]-pyridine,
3-(4-diethylaminophenylimino)-3H-[1,2,4]-thiadiazolo[4,3-a]-pyridine,
3-(5-methylisoxazol-3-ylimino)-3H-[1,2,4]-thiadiazolo[4,3-a]-pyridine,
3-(4,5-dihydrothiazol-2-ylimino)-3H-[1,2,4]-thiadiazolo[4,3a]-pyridine,
3-(1-benzylpiperidine-4-ylimino)-3H-[1,2,4]-thiadiazolo[4,3a]-pyridine,
3-(3-pyridinylimino)-3H-[1,2,4]-thiadiazolo-[4,3-a]-pyridine,
3-(4-t-butylphenylimino)-3H-[1,2,4]-thiadiazolo-[4,3-a]-pyridine,
3-(4-isopropoxyphenylimino)-3H-[1,2,4]-thiadiazolo[4,3-a]-pyridine,
3-(4-methylthiophenylimino)-3H-[1,2,4]-thiadiazolo[4,3-a]-pyridine, or
3-(4-pyrrolidinophenylimino)-3H-[1,2,4]-thiadiazolo[4,3-a]-pyridine.

4. Compound of claim 1, wherein the compound is
4-(3H-[1,2,4]-thiadiazolo[4,3-a]pyridin-3-ylideneamino)-phenylacetic acid N-(1H-tetrazol-5-yl)-amide,
3-(2-pyrimidinylimino)-3H-[1,2,4]-thiadiazolo-[4,3-a]-pyridine,
5-methyl-3-(4-pyridinylimino )-3H-[1,2,4]thiadiazolo[4,3-a]pyridine,
6-methyl-3-(4-pyridinylimino)-3H-[1,2,4]thiadiazolo[4,3-a]pyridine, or
8-methyl-3-(4-pyridinylimino)-3H-[1,2,4]-thiadiazolo[4,3-a]pyridine.

5. Compound of claim 1, wherein the compound is
3-(thiazol-2-ylimino)-3H-[1,2,4]-thiadiazolo-[4,3-a]-pyridine,
7-methyl-3-(4-pyridinylimino)-3H-[1,2,4]-thiadiazolo-[4,3-a]-pyridine,
6-chloro-3-(4-pyridinylimino)-3H-[1,2,4]-thiadiazolo[4,3-a]-pyridine,
3-phenylimino-3H-[1,2,4]-thiadiazolo[4,3-a]-quinoline, 3-(4-pyridinylimino-3H-[1,2,4]-thiadiazolo[4,3-a]-quinoline,
3-(4-methoxycarbonylmethylphenylimino)-3H-[1,2,4]-thiadiazolo[4,3-a]-pyridine,
4-(3H-[1,2,4]-thiadiazolo[4,3-a]-pyridin-3-ylideneamino)-phenylacetic acid hydrochloride, or
4-(3H-[1,2,4]-thiadiazolo[4,3-a]-pyridin-3-ylideneamino)-phenylacetic acid N-methylhydroxamide.

6. Pharmaceutical composition suitable for the treatment of allergic diseases comprising a compound of the formula

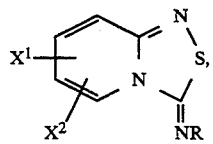

(I)

wherein
$X^1$ and $X^2$ are the same or different and independently are hydrogen, $C_2$-$C_6$ alkyl or halogen, or, if on adjacent ring carbon atoms, together with the adjacent ring carbon atoms, form a condensed phenyl ring, and
R is a radical selected from the group consisting of phenyl, cyclohexyl, cyclopentyl, pyridyl, piperidinyl, pyrimidinyl, pyrrolidinyl, isoxazolyl, oxazolyl, thiazolyl, thiazolinyl, triazolyl and tetrazolyl, which radical is unsubstituted or substituted at least once by halogen, cyano, nitro, $C_1$-$C_6$ alkyl, $C_1$-$C_6$ haloalkyl, hydroxyl, $C_1$-$C_6$ alkoxy, methylenedioxy, $C_1$-$C_6$-alkylthio, $C_1$-$C_6$ haloalkylthio, amino, $C_1$-$C_6$ alkylamino, $C_2$-$C_{12}$ dialkylamino, pyrrolyl, carboxyl, carbamoyl, benzyl, $C_1$-$C_6$ hydroxyalkyl, $C_2$-$C_7$ carboxyalkyl, $C_2$-$C_7$ alkoxycarbonyl-$C_1$-$C_6$-alkyl, carbamoyl-$C_1$-$C_6$-alkyl, N-hydroxy-N-$C_1$-$C_6$ alkyl carbamoyl-$C_1$-$C_6$-alkyl or $C_2$-$C_6$ alkenyl,
or a physiologically compatible salt thereof,
and a pharmaceutically acceptable carrier therefor.

7. A method of treating an allergic disease in a patient in need of such treatment, said method comprising administering is said patient an antiallergic effective amount of a compound of the formula

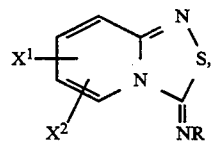

(I)

wherein $X^1$ and $X^2$ are the same or different and independently are hydrogen, $C_1$–$C_6$ alkyl or halogen, or, if on adjacent ring carbon atoms, together with the adjacent ring carbon atoms, form a condensed phenyl ring, and R is a radical selected from the group consisting of phenyl, cyclohexyl, cyclopentyl, pyridyl, piperidinyl, pyrimidinyl, pyrrolidinyl, isoxazolyl, oxazolyl, thiazolyl, thiazolinyl, triazolyl and tetrazolyl, which radical is unsubstituted or substituted at least once by halogen, cyano, nitro, $C_1$–$C_6$ alkyl, $C_1$–$C_6$ haloalkyl, hydroxyl, $C_1$–$C_6$ alkoxy, methylenedioxy, $C_1$–$C_6$-alkylthio, $C_1$–$C_6$ haloalkylthio, amino, $C_1$–$C_6$ alkylamino, $C_2$–$C_{12}$ dialkylamino, pyrrolyl, carboxyl, carbamoyl, benzyl, $C_1$–$C_6$ hydroxyalkyl, $C_2$–$C_7$ carboxyalkyl, $C_2$–$C_7$ alkoxycarbonyl-$C_1$–$C_6$-alkyl, carbamoyl-$C_1$–$C_6$-alkyl, N-hydroxy-N-$C_1$–$C_6$ alkyl carbamoyl-$C_1$–$C_6$-alkyl or $C_2$–$C_6$ alkenyl, or a physiologically compatible salt thereof.

* * * * *